United States Patent [19]

Chidsey, III et al.

[11] Patent Number: 4,596,812

[45] Date of Patent: * Jun. 24, 1986

[54] METHODS AND SOLUTIONS FOR TREATING MALE PATTERN ALOPECIA

[75] Inventors: Charles A. Chidsey, III, Boulder, Wyo.; Guinter Kahn, Miami Beach, Fla.

[73] Assignee: The Upjohn Company, Kalamazoo, Mich.

[*] Notice: The portion of the term of this patent subsequent to Feb. 13, 1996 has been disclaimed.

[21] Appl. No.: 181,959

[22] Filed: Aug. 28, 1980

Related U.S. Application Data

[63] Continuation of Ser. No. 708,374, Jul. 26, 1976, abandoned, which is a continuation of Ser. No. 470,962, May 17, 1974, abandoned, said Ser. No. 708,372, is a continuation-in-part of Ser. No. 689,473, May 24, 1976, abandoned, which is a continuation of Ser. No. 579,559, May 21, 1975, abandoned, which is a continuation of Ser. No. 396,820, Jul. 13, 1973, abandoned, which is a continuation of Ser. No. 213,743, Dec. 29, 1971, abandoned.

[51] Int. Cl.$^4$ .............................. A61K 31/505
[52] U.S. Cl. .................................. 514/256
[58] Field of Search .................. 424/251; 514/256

[56] References Cited

U.S. PATENT DOCUMENTS

| | | | |
|---|---|---|---|
| 3,270,015 | 8/1966 | Ursprung | 260/256.4 F |
| 3,382,247 | 5/1968 | Anthony et al. | 424/251 X |
| 3,382,248 | 5/1968 | Anthony et al. | 424/251 X |
| 3,461,461 | 8/1969 | Anthony et al. | 260/256.4 C |

*Primary Examiner*—Sam Rosen
*Attorney, Agent, or Firm*—Bruce G. Klaas; William G. Jameson

[57] ABSTRACT

This invention relates to the method for treating the form of alopecia commonly known as "male pattern baldness" which comprises regular topical application to the affected areas of the human scalp of a composition containing as at least one of its active ingredients 6-amino-1,2-dihydro-1-hydroxy-2-imino-4-piperidinopyrimidine. It also encompasses the aforesaid compound itself for use as a therapeutic agent to arrest and reverse male pattern alopecia.

14 Claims, No Drawings

METHODS AND SOLUTIONS FOR TREATING MALE PATTERN ALOPECIA

This application is a continuation of application Ser. No. 708,372, filed July 26, 1976, now abandoned, which is a continuation of application Ser. No. 470,964, filed May 17, 1974, now abandoned. Application Ser. No. 708,372, filed July 26, 1976, now abandoned, is also a continuation-in-part of application Ser. No. 689,473, filed May 24, 1976, now abandoned, which is a continuation of application Ser. No. 579,559, filed May 21, 1975, now abandoned, which is a continuation of application Ser. No. 396,820, filed July 13, 1973, now abandoned, which is a continuation of application Ser. No.213,743, filed Dec. 29, 1971, now abandoned. The benefit of all the foregoing filing dates are claimed herein.

BACKGROUND AND SUMMARY

The present invention relates to methods, compositions and solutions for treating male pattern alopecia involving the use of a substance known as "Minoxidil".

Dermatologists recognize many different types of hair loss, the most common by far being "alopecia" wherein human males begin losing scalp hair at the temples and on the crown of the head as they get older. While this type of hair loss is largely confined to males, hence its common name "male pattern baldness", it is not unknown in women. Be that as it may, no known cure has yet been found despite continuing attempts to discover one.

Notwithstanding the fact that nothing heretofore has been found which is effective in preventing, yet alone reversing, male pattern baldness, a good deal is known about various types of human hair and its growth patterns on various parts of the body.

For purposes of the present invention, we need only consider two types of hair, namely, "terminal hairs" and "vellus hairs". Terminal hairs are coarse, pigmented, long hairs in which the bulb of the hair follicle is seated deep in the dermis. Vellus hairs, on the other hand, are fine, thin, non-pigmented short hairs in which the hair bulb is located superifically in the dermis. As alopecia progresses, a transition takes place in the area of approaching baldness wherein the hairs themselves are changing from the terminal to the vellus type.

Another factor that contributes to the end result is a change in the cycle of hair growth. All hair, both human and animal, passes through a life cycle that includes three phases, namely, (1) the anagen phase (2) the catagen phase and (3) the telogen phase. The anagen phase is the period of active hair growth and, insofar as scalp hair is concerned, this generally lasts from 3-5 years. The catagen phase is a short transitional phase between the anagen and telogen phases which, in the case of scalp hair, lasts only 1-2 weeks. The final phase is the telogen phase which, for all practical purposes, can be denominated a "resting phase" where all growth ceases and the hair eventually is shed preparatory to the follicle commencing to grow a new one. Scalp hair in the telogen phase is also relatively short-lived, some 3-4 months elapsing before the hair is shed and a new one beings to grow.

Now, under normal hair growth conditions on the scalp, approximately 88% of the hairs are in the anagen phase, only 1% in catagen and the remainder in telogen. With the onset of male pattern baldness, a successively greater proportion of the hairs are in the telogen phase with correspondingly fewer in the active growth anagen phase.

The remaining result associated with alopecia is the severe diminution of hair follicles. A bald human subject will average only about 306 follicles per square centimeter, whereas, a non-bald one in the same age group (30-90 years) will still have an average of 460 follicles per square centimeter. This amounts to a one-third reduction in hair follicles which, when added to the increased proportion of vellus hair follicles and the increased number of hair follicles in telogen, is both significant and noticeable. It is written that approximately 50% of the hairs must be shed to produce visible thinning of scalp hair. It is thus a combination of these factors: (1) transition of hairs from terminal to vellus, (2) increased number of telogen hairs—some of which have been shed, and (3) loss of hair follicles (atrophy in Settel's description) that produces "baldness".

Now, while a good deal is known about the results of male pattern baldness, very little is known about its cause. About all that can be said is that the cause is felt to be genetic and hormonal in origin although, as will be seen presently, the known prior art attempts to control it through hormone adjustment have been singularly unsuccessful.

At the present time, one known treatment for male pattern alopecia is hair transplantation. Plugs of skin containing hair are transplanted from areas of the scalp where hair is growing to bald areas with reasonable success; however, the procedure is a costly one in addition to being time-consuming and quite painful. Furthermore, the solution is inadequate from the standpoint that it becomes a practical, if not an economic, impossibility to replace but a tiny fraction of the hair present in a normal healthy head of hair.

As far as the other non-drug related approaches to the problem are concerned, they include such things as ultra-violet radiation, massage, psychiatric treatment and exercise therapy. None of these, however, has been generally accepted as being effective. Even such things as revascularization surgery and acupuncture have shown little, if any, promise.

By far, the most common approach to the problem of discovering a remedy for male pattern alopecia has been one of drug therapy. Many types of drugs ranging from vitamins to hormones have been tried and only recently has there been any indication whatsoever of even moderate success. For instance, it was felt for a long time that since an androgenic hormone was necessary for the development of male pattern baldness, that either systemic or topical application of an antiandrogenic hormone would provide the necessary inhibiting action to keep the baldness from occurring. The theory was promising but the results were uniformly disappointing.

The androgenic hormone testosterone was known, for example, to stimulate hair growth when applied topically to the deltoid area as well as when injected into the beard and pubic regions. Even oral administration was found to result in an increased hair growth in the beard and pubic areas as well as upon the trunk and extremities. While topical application to the arm causes increased hair growth, it is ineffective on the scalp and some thinning may even result. Heavy doses of testosterone have even been known to cause male pattern alopecia.

Certain therapeutic agents have been known to induce hair growth in extensive areas of the trunk, limbs and even occasionally on the face. Such hair is of intermediate status in that it is coarser than vellus but not as coarse as terminal hair. The hair is generally quite short with a length of 3 cm. being about maximum. Once the patient ceases taking the drug, the hair reverts to whatever is normal for the particular site after six months to a year has elapsed. An example of such a drug is diphenylhydantoin which is an anticonvulescent drug widely used to control epileptic seizures. Hypertrichosis is frequently observed in epileptic children some two or three months after starting the drug and first becomes noticeable on the extensor aspects of the limbs and later on the trunk and face. The pattern is not unlike that sometimes caused by injury to the head. As for the hair, it is often shed when the drug is discontinued but may, in some cicumstances, remain.

Streptomycin is another drug that has been found to produce hypertrichosis in much the same way as diphenylhydantoin when administered to children suffering from tuberculous meningitis. About the same effects were observed and the onset and reversal of the hypertrichosis in relation to the period of treatment with the antibiotic leave little question but that it was the causative agent.

Of all the drug therapy resulting in hypertrichosis, the only two treatments known to applicants which have been demonstrated as showing some promise in reversing male pattern alopecia are the use of a microemulsion cream containing both estradiol and oxandrolone as its active ingredients and the use of organic silicon. The latter work is being done in Russia and little is known about it other than that considerable success has been claimed on both animal and human subjects in preliminary studies. The other work is being done here in the United States by Dr. Edward Settel who feels his cream is an efective agent to stimulate dormant hair follicles but not those that have atrophied.

While both of the above treatments show some promise and are the only ones revealed in the literature to have grown hair through topical application to the scalp of a human being suffering from male pattern baldness, the drugs themselves are far different from that which applicants have found effective for this same purpose, namely, 6-amino-1,2-dihydro-1-hydroxy-2-imino-4-piperidinopyrimidine. The compound itself was discovered by William C. Anthony and Joseph J. Ursprung and it forms the subject matter among other similar compounds of U.S. Pat. No. 3,461,461 issued Aug. 12, 1969. This compound, among others, has proven to have considerable therapeutic value in the treatment of severe hypertension. It is a so-called "vasodilator" which, as the name implies, functions to dilate the peripheral vascular system.

Vasodilators as a general class of therapeutic agents have, so far as applicants are aware, never proven effective to grow hair on the scalp as a result of topical application thereof to bald areas. Accordingly, the present invention relates to the unobvious and completely unexpected discovery that male pattern alopecia can be effectively treated by repeated topical application of a composition containing as one of its active ingredients 6-amino-1,2-dihydro-1-hydroxy-2-imino-4-piperodinopyrimidine, hereinafter to be referred to by the coined term "Minoxidil" to affected areas of the human scalp.

As disclosed in U.S. Pat. No. 3,461,461, Minoxidil comprises a compound of the formula:

"6-amino -1,2-dihydro-1-hydroxy-2-iminopyrimidines, their carboxyacylated counterparts, and the corresponding acid addition salts thereof are disclosed. The compounds, useful inter alia as antihypertensive agents, are substituted in the 4-position and optionally in the 5-position, the substituent in the 4-position being a secondary or tertiary amino moiety."

It is, therefore, the principal object of the present invention to provide a novel and effective treatment for male pattern baldness.

Another object of the invention forming the subject matter hereof is to provide a method of treating certain types of baldness in humans that is compatible with various types of therapeutic agents or carriers and, therefore, would appear to be combinable with those which, by themselves, demonstrate some therapeutic activity such as, for example, Dr. Settel's microemulsion cream containing estradiol and oxandrolone or, alternatively, perhaps the organic silicon developed in Russia.

Still another objective is the provision of a treatment for alopecia which, while effective for its intended purpose, is apparently non-toxic and relatively free of unwanted side effects.

An additional object of the invention herein disclosed and claimed is to provide a method for treating baldness in men which can be applied by the patient himself under medical supervision no more stringent than that demanded for other topically-administered therapeutic agents.

Other objects of the invention are to provide a treatment for male pattern alopecia which is safe, simple, painless, cosmetic in the sense of being invisible, easy to apply and quite inexpensive when compared with hair transplants and the like.

Further objects will be in part apparent and in part pointed out specifically hereinafter in connection with the detailed description of the invention which follows.

Dermatologists and others were well aware of the fact that prolonged vasodilation of certain areas of the human body other than the scalp sometimes resulted in increased hair growth even in the absence of any vasodilating therapeutic agent. For instance, increased hair growth around surgical scars is not uncommon. Similarly, arteriovenous fistula have been known to result in increased vacularity accompanied by enhanced hair growth. Externally-induced vasodilation of the skin, such as, for example, by repeated biting of the limbs by mental retardates and localized stimulation of the shoulders by water carries has been noted to bring on hypertrichosis in the affected areas. Be that as it may, similar techniques such as continued periodic massage of the scalp have been found totally ineffective as a means for restoring lost hair growth to the scalp. Scar tissue on the scalp inhibits rather than promotes hair growth.

"Minoxidil", as was true with "Diazoxide", produced a good deal of hypertrichosis in patients to whom the drug was administered. See, for example, of Journal of Laboratory and Clinical Medicine, Vol. 79, page 639, April, 1972; Circulation, Vol. 45, page 571, March 1972; and Clinical Pharmacy and Therapy, Vol. 13, page 436, 1972. In fact, it caused rather profuse hair growth on many parts of the body, specifically, the trunk, extremities, beard and scalp. Even women grew a good deal of facial as well as body hair. Men, on the other hand, had thicker beards and were forced to shave more often. While some hair growth was noted on the scalp, it was accompanied by hair growth on other areas of the body which, for some men at least, would be considered more detrimental to their appearance than any gains that were made in the bald areas on the scalp. For women especially, this unwanted profuse growth of facial and body hair constitutes a serious side effect of the drug that would severely limit its practical utility in all but the most critical applications where the overall well being of the patient outweighted this disadvantage.

DETAILED DESCRIPTION

Test 1

Applicant's first tests involved topical applications of both "Diazoxide" and "Minoxidil" to the deltoid area of the human body. Four MNX* solutions were used as follows:

1% MNX in Dimethylacetamine (DMA) *MNX abbr. for "Minoxidil"
1% MNX in equal parts of DMA and ethyl alcohol
½% MNX in equal parts of ethyl alcohol and propylene glycol
1% MNX in equal parts of ethyl alcohol and propylene glycol The "Diazoxide" solutions were as follows:
1% Diazoxide in ethyl alcohol
2% Diazoxide in ethyl alcohol Daily topical applications of the MNX solutions by way of contact occlusion to the deltoid areas were made while the solvents alone were similarly topically applied to other deltoid areas. Four out of five areas so treated showed evidence of increased hair growth by 7 weeks. The hair was both larger and coarser in the treated area. The only failure demonstrated an irritant reaction to the solvent, not the active ingredient. No detectable difference was noted between the ½% and the 1% MNX solutions. The hair remained so long as the treatment continued, however, when it was discontinued, the hair fell out and the treated area returned to normal within a three month period. The use of "Minoxidil" continued for a period of 4 months although the patient's progress continued to be monitored for some 11 months. Biopsies indicated that the treatment had activated vellus hairs to become terminal hairs. There appeared to be no evidence of systemic absorption as the patient's blood pressure and pulse remained unchanged. Most significant was the fact that the increased hair growth was confined to the treated areas contrary to the results found when MNX was administered internally.

The Diazoxide tests were a failure in the sense that no increased hair growth was noted.

Test 2

The first subject was a 28 year old male who historically had suffered from male pattern alopecia for a period of ten years. He was treated with twice daily topical applications of MNX to the scalp for a period of just over seven months. The solution used contained 2% MNX dissolved in equal parts of ethyl alcohol and propylene glycol. The dosage used was ½ cc. at each application and the patient used a shower cap occlusion overnight to increase penetration. At the end of 4 weeks there was no observable change, however, by the 12th week there was a definite subjective increase and by the 20th week both a subjective and objective increase was observed.

During the test period, the subject showed no change in blood pressure or pulse rate. Several months after the treatment was discontinued, the new growth of scalp hair fell out.

Test 3

The other human subject was a 30 year old male who had also been afflicted for some 10 years with male pattern alopecia. The same solution was used for the second patient as the first and the same dosage and schedule prescribed, however, the second patient was not as faithful as the first and probably averaged no more than a single application a day, if that, over a test period of seven months.

When the patient was examined at the end of 4 and 8 weeks, no change was seen. At 12, 16 and 20 weeks, a slight increase in hair growth was noted on the bald areas of the scalp which were topically treated with the MNX solution, however, the real effect the drug had on the patient became most dramatically apparent following discontinuation of the therapy when the new growth of hair fell out and the difference was most noticeable. Here again, no change in either blood pressure or pulse rate was noted.

The foregoing tests clearly demonstrate its completely unexpected ability to not only arrest, but reverse, male pattern alopecia.

Test 4

For 7 weeks 1% Minoxidil solution was applied to an area about 2.5 cm in diameter of the upper outer arm and of the frontal area of baldness i.e. the executive corner of the scalp, while similar placebo material without the Minoxidil was applied to the other side. This was followed for the next 7 weeks by the application of 5% Minixodil solution in a similar manner. The areas were covered by plastic occulsion after each application every day. On the scalp collodion covered the edge of the plastic to keep the application occlusive, while on the upper outer arm colostomy type edges covered the plastic to form the occlusive area there. In other words, collodion provided the occlusivity of the ring around the plastic on the scalp while the colostomy provided the occulusivity to the saran wrap on the upper outer arm. There were no side effects from this method of delivery except from irritation of the vehicle as noted in control sites also.

Of the 13 patients who completed the study, growth of hair was noted on the upper outer arm in 12. Growth of hair on the forehead-scalp region in 5. The growth began at approximately 7 weeks in all of the patients who had hair growth. In other words growth began at about the beginning of the use of the 5% solution.

In summary, the topical use of "Minoxidil" definitely will effect increased human hair growth when applied to the human skin including the scalp where it is effective to not only arrest, but reverse, male pattern alopecia. It has been established that best results are obtained by daily occluded topical application for a period of time sufficient to effect hair growth. Occlusion of the solution may be obtained by any conventional means such as bandages, plastic coverings, shower caps, swimming caps, etc. The test results have shown that ½% to 5% "Minoxidil" solutions are effective and it appears that the percentage of "Minoxidil" in solution may be varied as necessary or desirable to achieve the desired results.

Thus, it is intended that modifications and variations of the present invention, which have been hereinbefore disclosed or suggested, be included within the scope of the appended claims except insofar as limited by the prior art.

Accordingly the present invention provides:

A topical pharmaceutical composition for treating male pattern alopecia comprising a physiologically effective amount of 6-amino-1,2-dihydro-1-hydroxy-2-imino-4-piperidinopyrimidine dissolved in a non-toxic solvent.

A topical pharmaceutical composition for treating male pattern alopecia comprising a physiologically effective amount of 6-amino-1,2-dihydro-1-hydroxy-2-imino-4-piperidinopyrimidine dissolved in a non-toxic solvent selected from the group consisting of dimethylacetamide, ethyl alcohol, and propylene glycol.

A topical pharmaceutical composition for treating male pattern alopecia comprising a physiologically effective amount of 6-amino-1,2-dihydro-1-hydroxy-2-imino-4-piperidinopyrimidine dissolved in a non-toxic solvent, wherein the concentration 6-amino-1,2-dihydro-1-hydroxy-2-imino-4-piperidinopyrimidine is ¼% to 5%.

A composition comprising ¼% to 5% of 6-amino-1,2-dihydro-1-hydroxy-2-imino-4-piperidinopyrimidine and a solvent for use by topical application to the human scalp to promote the growth of human hair.

The invention claimed is:

1. A method of treating humans for alopecia which comprises topically applying to the human scalp an effective amount of a solution containing 6-amino-1,2-dihydro-1-hydroxy-2-imino-4-piperidinopyrimidine and a solvent.

2. The method as defined in claim 1 wherein the said solution comprises 1% of 6-amino-1,2-dihydro-1-hydroxy-2-imino-4-piperidinopyrimidine in dimethylacetamide.

3. The method as defined in claim 1 wherein said solution comprises 1% of 6-amino-1,2-dihydro-1-hydroxy-2-imino-4-piperidinopyrimidine in equal parts of dimethylacetamide and ethyl alcohol.

4. The method as defined in claim 1 wherein said solution comprises ¼% of 6-amino-1,2-dihydro-1-hydroxy-2-imino-4-piperidinopyrimidine in equal parts of ethyl alcohol and propylene glycol.

5. The method as defined in claim 1 wherein said solution comprises 1% of 6-amino-1,2-dihydro-1-hydroxy-2-imino-4-piperidinopyrimidine in equal parts of ethyl alcohol and propylene glycol.

6. The method as defined in claim 1 and wherein said solution comprises 2% of said 6-amino-1,2-dihydro-1-hydroxy-2-imino-4-piperidinopyrimidine in equal parts of ethyl alcohol and propylene glycol.

7. The method as defined in claim 1 and wherein said solvent is selected from the group consisting of dimethylacetamide, ethyl alcohol and propylene glycol.

8. The method as defined in claim 1 and wherein the concentration of 6-amino-1,2-dihydro-1-hydroxy-2-imino-4-piperidinopyrimidine is ¼% to 5%.

9. The method of arresting and reversing male pattern alopecia which comprises continued periodical topical application to the human scalp of a physiologically effective dose of 6-amino-1,2-dihydro-1-hydroxy-2-imino-4-piperidinopyrimidine dissolved in a solvent.

10. The method as defined in claim 9 wherein said solvent is selected from the group consisting of ethyl alcohol, propylene glycol and dimethylacetamide.

11. The method of claim 9 wherein the 6-amino-1,2-dihydro-1-hydroxy-2-imino-4-piperidinopyrimidine is present in the solution in an amount of 0.5% to 2.0%.

12. The invention of any one of claims 1-11 and wherein the method further comprises occlusion of the effective amount of the solution after application to the human scalp for a period of time sufficient to effect hair growth.

13. In a pharmaceutical composition containing minoxidil in solution, the improvement characterized by:
a vehicle which adapts said composition for topical application to the human scalp for the treatment of alopecia, said minoxidil being dissolved in said composition in a concentration of from about 0.5% to about 5.0%.

14. A topical pharmaceutical solution for the treatment of alopecia consisting essentially of:
(a) from about 0.5% to about 5.0% minoxidil of said solution, and
(b) a vehicle which adapts said solution for topical application to the human scalp.

* * * * *

UNITED STATES PATENT OFFICE
CERTIFICATE OF CORRECTION

Patent No. 4,596,812          Dated 24 June 1986

Inventor(s) Charles A. Chidsey and Guinter Kahn

It is certified that error appears in the above-identified patent and that said Letters Patent are hereby corrected as shown below:

On the title page

[63] "Continuation of Ser. No. 708,374 Jul. 26, 1976, abandoned, which is a continuation of Ser. No. 470,962..." should read: -- Continuation of application Serial No. 708,372, filed July 26, 1976, now abandoned, which is a continuation of application Serial No. 470,964... --.

Column 4, line 51: "carries" should read -- carriers --.

Column 4, line 59: "of Journal of" should read: -- Journal of --.

Signed and Sealed this

Ninth Day of December, 1986

*Attest:*

DONALD J. QUIGG

*Attesting Officer*      *Commissioner of Patents and Trademarks*